US00PP22566P2

(12) United States Plant Patent
Hall

(10) Patent No.: US PP22,566 P2
(45) Date of Patent: Mar. 6, 2012

(54) LAVENDER PLANT NAMED 'VANESSA LEIGH'

(50) Latin Name: *Lavandula stoechas*
Varietal Denomination: Vanessa Leigh

(76) Inventor: Elsie Kazerine Hall, Wairau Valley (NZ)

( * ) Notice: Subject to any disclaimer, the term of this patent is extended or adjusted under 35 U.S.C. 154(b) by 0 days.

(21) Appl. No.: 12/807,674

(22) Filed: Sep. 10, 2010

(51) Int. Cl.
*A01H 5/00* (2006.01)

(52) U.S. Cl. ..... Plt./445

(58) Field of Classification Search ..... Plt./445
See application file for complete search history.

*Primary Examiner* — Susan McCormick Ewoldt

(57) ABSTRACT

A new cultivar of Lavender plant named 'Vanessa Leigh' that is characterized by dark violet flowers, violet terminal bracts, flowers having a musk fragrance and dark green foliage.

1 Drawing Sheet

Botanical classification: *Lavandula stoechas.*
Variety denomination: 'Vanessa Leigh'.

BACKGROUND OF THE INVENTION

The present invention relates to a new and distinct cultivar of Lavender plant botanically known as *Lavandula stoechas* and hereinafter referred to by the cultivar name 'Vanessa Leigh'.

The new cultivar was discovered in 2005 as a single plant in a bed of *Lavandula stoechas* plants in a cultivated area of Wairau Valley, New Zealand. The exact parent plants are unknown.

Asexual reproduction of the new cultivar 'Vanessa Leigh' by terminal cuttings was first performed in 2005 in Wairau Valley, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new Lavender cultivar 'Vanessa Leigh'. These traits in combination distinguish 'Vanessa Leigh' as a new and distinct cultivar.

1. Lavender 'Vanessa Leigh' exhibits dark violet flowers with violet terminal bracts.
2. Lavender 'Vanessa Leigh' exhibits flowers having a musk fragrance.
3. Lavender 'Vanessa Leigh' exhibits dark green foliage.

The closest comparison varieties are Lavender 'Helmsdale' (not patented) and Lavender 'Quasti' (not patented).

'Vanessa Leigh' is different than 'Helmsdale' in having lighter violet terminal bracts, darker green leaves and a less compact habit.

'Vanessa Leigh' is different than 'Quasti' in having darker violet flowers, darker green leaves and a less compact habit.

BRIEF DESCRIPTION OF THE DRAWING

The accompanying photograph illustrates the distinguishing traits of Lavender 'Vanessa Leigh'. The plant in the photograph shows an overall view of a 12 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new Lavender cultivar named 'Vanessa Leigh'. Data was collected in Wairau Valley, New Zealand from 12 month old field grown plants. The time of year was Summer and the average temperature was 20 to 32° Centigrade during the day and 9 to 18° Centigrade at night. Color determinations are in accordance with The Royal Horticultural Society Colour Chart 2001 edition, except where general color terms of ordinary dictionary significance are used. The growing requirements are similar to the species. 'Vanessa Leigh' has not been tested under all possible conditions and phenotypic differences may be observed with variations in environmental, climatic, and cultural conditions, however, without any variance in genotype.

Botanical classification: Lavender stoechas 'Vanessa Leigh'.
Use: Ornamental Perennial.
Parentage: The exact parent plants of 'Vanessa Leigh' are unknown.
Vigor: Moderate.
Container size: 9 cm. and larger.
Growth habit: Upright, outwardly spreading.
Plant shape: Rounded with erect flower spikes.
Height: Average 30 cm. in height.
Width: Average 50 cm. in width.
Hardiness: −9° to 38° C.
Propagation: Terminal cuttings.
Crop time: 9 months.
Stem:
- *Branching habit.*—Free branching.
- *Number of lateral branches.*—*Approximately* 50.
- *Lateral branch diameter.*—3 mm. in diameter.
- *Lateral branch length.*—24 cm. in length.
- *Lateral branch strength.*—Strong.
- *Color.*—195A.
- *Pubescence.*—Lightly covered with short hairs.
- *Internode length.*—2.5 cm. between nodes.
- *Shape.*—Round.

Foliage:
- *Leaf arrangement.*—Opposite.
- *Compound or single.*—Single.

*Leaf shape.*—Linear.
*Leaf apex.*—Acute.
*Leaf base.*—Rounded.
*Leaf length.*—4.0 cm. in length.
*Leaf width.*—3.0 mm. in width.
*Texture.*—Velvety.
*Pubescence.*—Present.
*Leaf margin.*—Entire.
*Vein pattern.*—Alternate.
*Young leaf color* (*upper surface*).—148C.
*Young leaf color* (*lower surface*).—148C.
*Mature leaf color* (*upper surface*).—148C.
*Mature leaf color* (*lower surface*).—148C.
*Leaf attachment.*—Sessile.

Flower:
*Flower arrangement.*—Flowers arranged on cylindrical spikes.
*Inflorescence dimensions.*—4.0 cm. in length and 2.5 cm. in diameter.
*Quantity of flowers and buds per inflorescence.*—Approximately 55.
*Flowering season.*—Spring to Summer.
*Time to flower or response time.*—4 to 6 weeks after buds form.
*Fragrance.*—Musk scent.
*Self-cleaning or persistent.*—Self cleaning.
*Flower bud length.*—25 mm. in length.
*Flower bud diameter.*—12 mm. in diameter.
*Flower bud shape.*—Ovate.
*Bud color.*—N79C.
*Flower aspect.*—Outward.
*Flower dimensions.*—10 mm. in diameter and 24 mm. in height.
*Flower longevity.*—Lasts approximately 20 to 25 days.
*Petal arrangement.*—Five fused into a tube.
*Petal shape.*—Oblanceolate.
*Petal margin.*—Entire.
*Petal apex.*—Truncate.
*Petal texture.*—Smooth.
*Petal dimensions.*—28 mm. in length and 9 mm. in width.
*Petal color when opening* (*upper side*).—N79D.
*Petal color when opening* (*under side*).—N79D.
*Petal color when fully opened* (*upper side*).—N79D.
*Petal color when fully opened* (*under side*).—N79D.
*Petal color fading to.*—N82D.

Calyx:
*Calyx dimensions.*—2.5 mm. in length and 1.5 mm. in diameter.

Sepal:
*Sepal number.*—16.
*Sepal shape.*—Elliptic.
*Sepal margin.*—Entire.
*Sepal apex.*—Acute.
*Sepal base.*—Cuneate.
*Sepal dimensions.*—4 mm. in length and 7 mm. in width.
*Sepal color when opening* (*upper side*).—84D.
*Sepal color when opening* (*under side*).—138D.
*Sepal color when fully opened* (*upper side*).—84D.
*Sepal color when fully opened* (*under side*).—138D.

Peduncle:
*Peduncle dimensions.*—28 cm. in length and 2 mm. in diameter.
*Peduncle angle.*—Vertical.
*Peduncle color.*—148D.
*Peduncle strength.*—Strong.

Fruit and seed production: Plants of the new Lavender have not been observed for fruit and seed production.

Disease and pest resistance: Plants of the new Lavender have not been observed for disease or pest resistance.

The invention claimed is:

1. A new and distinct variety of Lavender plant named 'Vanessa Leigh' as described and illustrated.

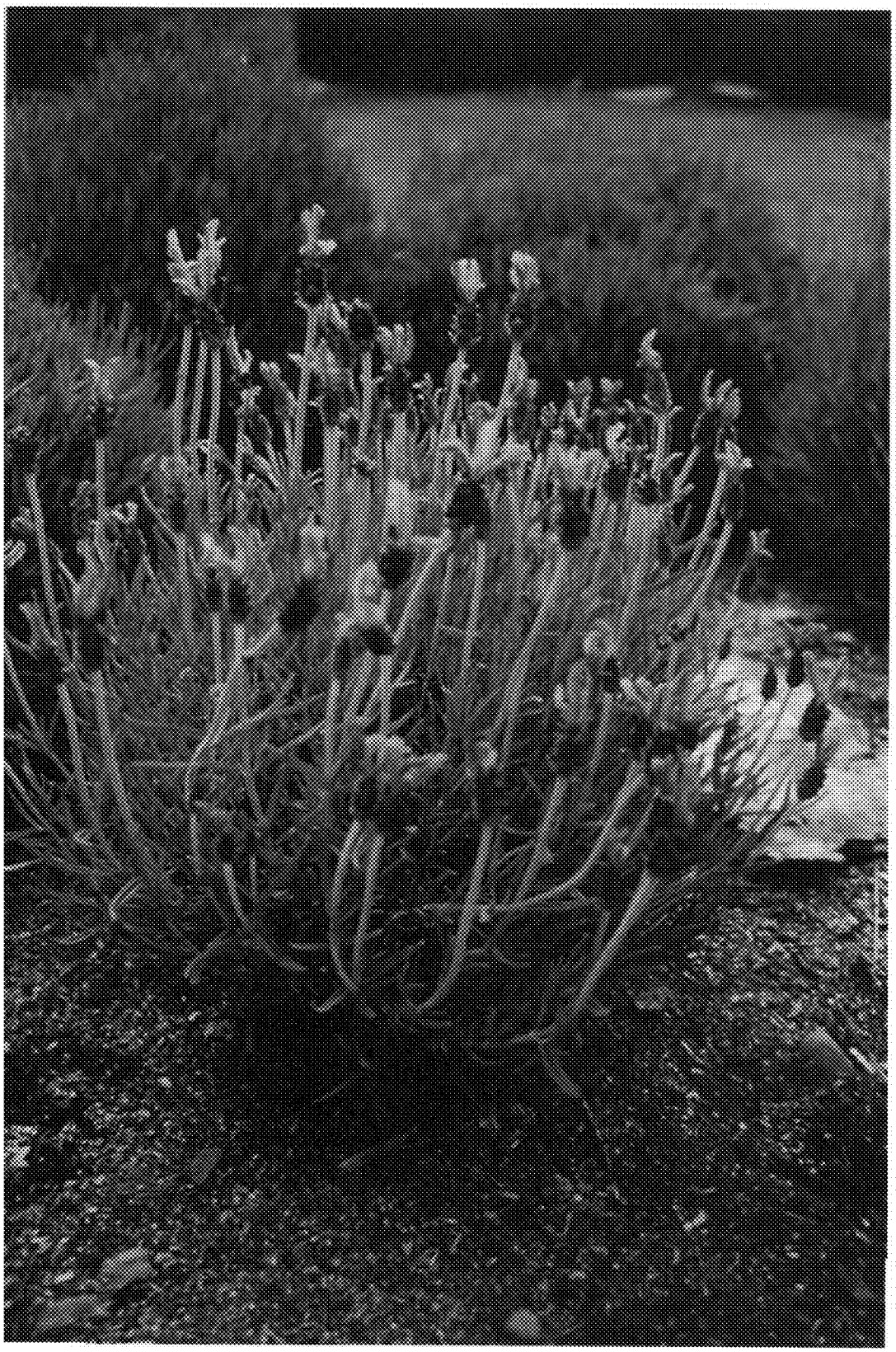

* * * * *